United States Patent [19]

Boyle et al.

[11] Patent Number: 5,098,827
[45] Date of Patent: Mar. 24, 1992

[54] NOVEL BACTERIAL MARKERS FOR PATHOGENIC GROUP B STREPTOCOCCI

[75] Inventors: Michael D. P. Boyle; L. J. Brady, both of Gainesville, Fla.

[73] Assignee: The University of Florida, Gainesville, Fla.

[21] Appl. No.: 160,616

[22] Filed: Feb. 26, 1988

[51] Int. Cl.$^5$ .................. G01N 33/569; G01N 33/53; C12Q 1/14
[52] U.S. Cl. .................. 435/7.34; 435/7.32; 435/7.9; 435/35; 435/36; 435/39; 435/810; 435/820; 435/885; 435/7.2; 436/501; 436/518; 436/804; 436/808; 530/415; 530/825; 530/389.5
[58] Field of Search .................. 435/7.29, 35, 36, 39, 435/810, 820, 885, 7.2, 7.9, 7.32, 7.34; 436/501, 518, 804, 808; 530/415, 825, 387

[56] References Cited

PUBLICATIONS

Oellerich, M., J. Clin. Chem. Clin. Biochem., vol. 22(12), pp. 895-904 (1984).
The Sigma Chemical Company Catalog, pp. 1142-1144 (1987).
Mueller et al., *Chemical Abstracts*, vol. 110(15): 121798d (1989).
Waltonen et al., *Microbial Pathogenesis*, vol. 1, pp. 191-204 (1986).
Jackson et al., Abstracts of the 87th Annual Meeting of the Amerian Society for Microbiology, p. 50 (1987).
Kasper et al., *Chemical Abstracts*, vol. 108(15):130073k (1988).
Brady et al., The Journal of *Infectious Diseases*, vol. 158 (5), pp. 965-972 (1988).
Jelinkova, J. (1977) "Group B Streptococci in the Human Population," Current Topics in Microbiology and Immunology 76:127-165.
Lim, D. V., W. J. Morales, A. F. Walsh and D. Kazanis (1986) "Reduction of Morbidity and Mortality Rates for Neonatal Group B Streptoccal Disease through Early Diagnosis and Chemoprophylaxis," J. Clin. Micro. 23:489-492.
Boyer, K. M. and S. P. Gotoff (1986) "Prevention of Early-Onset Neonatal Group B Streptococcal Disease with Selective Intrapartum Chemoprophylaxis," New England J. Med. 314:1665-1669.
Russell-Jones, G. J., E. C. Gotschlinch, and M. S. Blake (1984) "A Surface Receptor Specific for Human IgA on Group B Streptococci Possessing the Ibc Protein Antigen," J. Exp. Med. 160:1467-1475.
Russell-Jones, G. J. and E. C. Gotschlich (1984) "Identification of Protein Antigens of Group B Streptococci, with Special Reference to the Ibc Antigens," J. Exp. Med. 160:1476-1484.

*Primary Examiner*—Esther L. Kepplinger
*Assistant Examiner*—Toni R. Scheiner
*Attorney, Agent, or Firm*—Saliwanchik & Saliwanchik

[57] ABSTRACT

The subject invention concerns a novel in vitro process for identifying and quantifying native antigens on potentially pathogenic group B streptococci bacteria present in a clinical specimen. The invention process is made possible by the discovery of novel bacterial markers denoted γ and δ epitopes which are expressed by a variety of group B streptococcal strains.

19 Claims, 4 Drawing Sheets

NOVEL BACTERIAL MARKERS FOR PATHOGENIC GROUP B STREPTOCOCCI

BACKGROUND OF THE INVENTION

Group B streptococci (GBS) are being increasingly recognized as important human pathogens. In addition to causing meningitis, bacteremia, endocarditis, bronchopneumonia, arthritis, peritonitis, wound infections, abscesses, and urinary tract infections in adults, as many as 80% of group B infections occur in neonates (Jelinkova, J. [1977] Current Topics in Microbiology and Immunology 76:127-165). Approximately 30% of pregnant women have been reported to be colonized by GBS. Despite this high carriage rate, neonatal infection occurs with an incidence of only 0.5%, resulting in over 12,000 deaths annually (Lim, D. V., Morales, W. J., Walsh, A. F., and Kazanis, D. [1986] J. Clin. Micro. 23:489-492). Predisposing factors to development of disease are premature birth, prolonged rupture of membranes, overt maternal infection, and deficiency of type specific antibody (Boyer, K. M. and Gotoff, S. P. [1986] New England J. Med. 314:1665-1669). To date no one has identified a bacterial marker which would predict which streptococcal strains are more likely to cause infection.

The ability to subtype group B streptococci more comprehensively may be of value in predicting which organisms could cause sepsis, in particular neonatal sepsis. Recently, a receptor for the Fc region of human IgA was reported to be expressed on the surfaces of some strains of GBS (Russell-Jones, G. J., Gotschlich, E. C., and Blake, M. S. [1984] J. Exp. Med. 160:1467-1475). Western blot analysis of proteins extracted from these strains by treatment with detergent indicated that it may in fact be the β antigen component of the c protein marker complex which has the ability to bind to IgA (Russell-Jones, G. J. and Gotschlich, E. C. [1984] J. Exp. Med. 160:1476-1484). Since IgA is the primary line of defense at mucosal surfaces, such as the vaginal epithelium, the ability of bacteria to bind this class of immunoglobulin molecules in a non-immune fashion might interfere with effective clearance of these microorganisms.

A further level of sub-typing of group B streptococci, with respect to the c protein marker complex, would be desirable to identify potential pathogens.

BRIEF SUMMARY OF THE INVENTION

This invention concerns novel bacterial markers which can be used to identify potentially pathogenic neonatal organisms. More specifically, the subject invention concerns novel bacterial markers denoted gamma and delta ($\gamma$ and $\delta$) epitopes which can be used to classify further group B streptococci. These novel epitopes are expressed by a variety of group B streptococcal strains. Many of the group B streptococcal strains also express the known $\alpha$ and $\beta$ antigens within the c protein marker complex. The group B streptococcal strain denoted A909, which is the international typing strain available from the ATCC repository at 12301 Parklawn Drive, Rockville, Md., as ATCC 27591, can be used to express the known antigens $\alpha$ and $\beta$, and the novel antigens of the subject invention, $\gamma$ and $\delta$.

The discovery of the novel epitopes of the invention was enabled by a rapid two-stage radioimmunoassay (RIA) which identifies type specific antigens on the surfaces of group B streptococci. This improved rapid technique detects native unmodified type specific antigens on bacterial surfaces objectively and economically with results obtained within three hours. The assay utilizes intact bacteria and does not require hot acid extraction. Consequently, this method detects acid stable as well as acid-labile antigens in their native unmodified form. The RIA is semi-quantitative and uses the same type specific antisera as precipitin testing. The classical precipitin test is dependent on optimal concentrations of both antigens and antibodies for precipitation to occur resulting in the potential for false negative results. In addition, hot acid extraction procedures have the potential to change the native configuration of the bacterial antigenic determinants. These problems are not encountered with the more sensitive RIA procedure.

DETAILED DESCRIPTION OF THE INVENTION

MATERIALS AND METHODS

Bacterial Strains, Media and Growth Conditions

Figure 1:
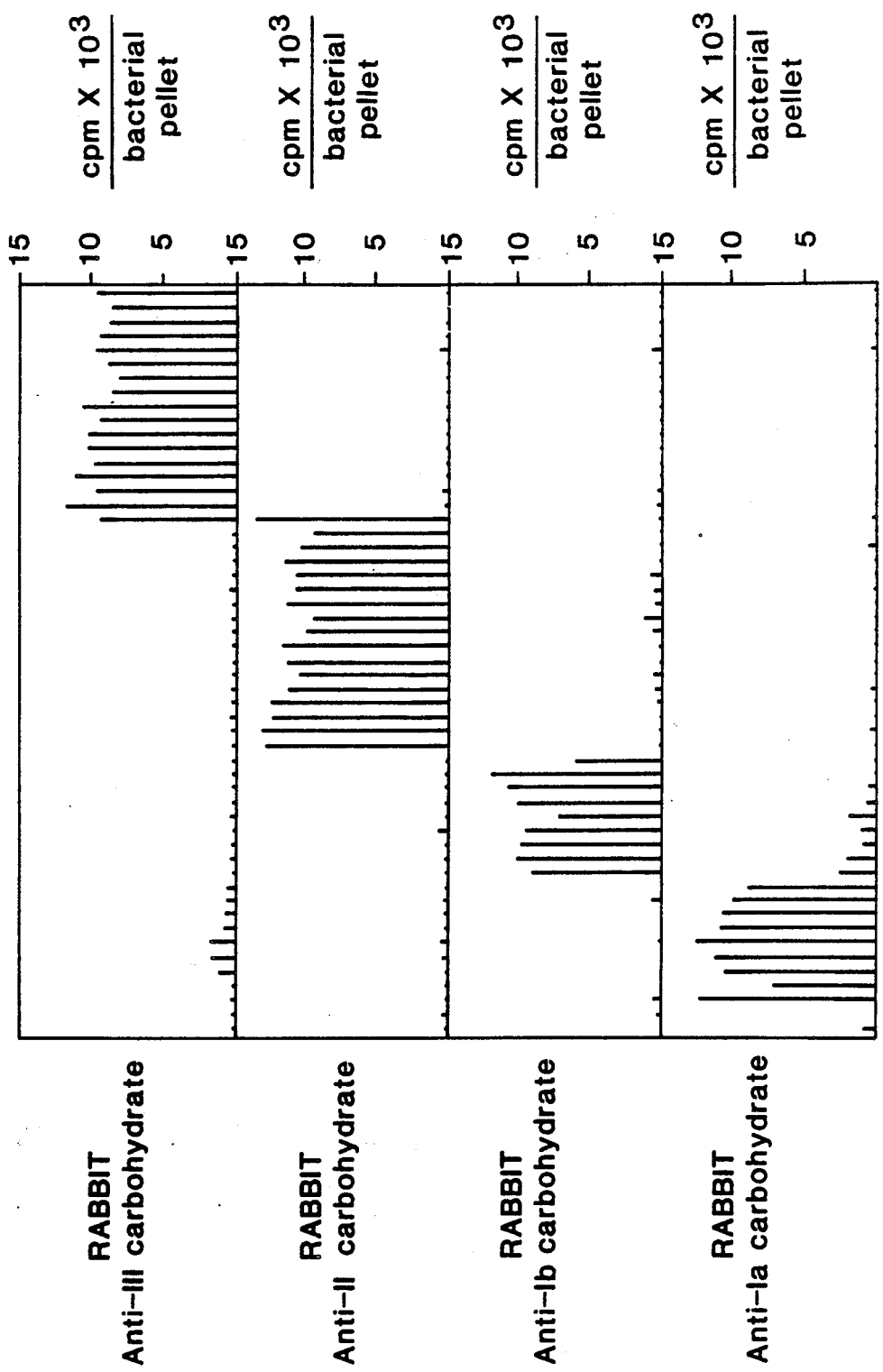
FIG. 1: Analysis of type specific carbohydrate antigens on the surface of group B streptococci.

Laboratory strains of group B streptococci were used. All strains were confirmed as group B streptococci by screening with the Phadebact Streptococcus Test (Pharmacia Diagnostics, Piscataway, N.J.). Bacteria were grown as stationary cultures in Todd-Hewitt broth (Difco, Detroit, Mich.) for 18-24 hr at 37° C. The bacteria were harvested by centrifugation and washed in 0.15M phosphate buffered saline (PBS), pH 7.2. Stock cultures were stored in glycerol at −70° C. Sodium azide was added to a final concentration of 0.02% to stored culture supernatants.

Source of Group B Streptococci Typing Antiserum

Rabbit anti-type Ia, Ib, II, and III carbohydrate antigens, as well as rabbit anti-c protein antigen, were kindly provided by Dr. R. Facklam, Center for Disease Control, Atlanta, Ga.

Adsorption of Anti-c Protein Typing Antiserum

Bacterial strains expressing the reactivities to be depleted from the anti-c antiserum were chosen as appropriate adsorbents after characterization in the two-stage RIA described below. The bacteria from 5 ml of a Todd-Hewitt broth overnight culture were pelleted by centrifugation and washed once with 2 ml of PBS, pH 7.2. A 100 µl sample of anti-c protein antiserum was added to the washed bacterial pellet and rotated at 4° C. for 1 hour. The adsorption was repeated at least twice or until all reactivity against the adsorbing strain was eliminated as detected by the two-stage RIA.

Source of Protein A

The type I bacterial Fc receptor, staphylococcal Protein A, was purchased from Pharmacia Fine Chemicals, Piscataway, N.J.

Iodination of Protein A

Protein A was radioiodinated by the mild lactoperoxidase method using Enzymobeads (Bio-Rad, Richmond, Calif.) (Reis, K. J., Ayoub, E. M., and Boyle, M. D. P. [1983] J. Immunol. Meth. 59:83-94). The labeled protein was separated from free iodine by passage over a G25 column (PL 10, Pharmacia) and collected in veronal buffered saline, pH 7.4 containing 0.001M $Mg^{++}$, 0.00015M $Ca^{++}$, and 0.1% gelatin (VBS gel, Reis et al., supra). Proteins labeled by this method routinely have a specific activity of approximately 0.3 mCi/mg (Reis et al. supra).

Hot Acid Extracts of Group B Streptococci

Laboratory strains to be hot acid extracted were inoculated into 10 ml Todd-Hewitt broth starter culture tubes. After 6-8 hours of growth the cultures were transferred to vessels containing 150 ml of sterile Todd-Hewitt broth and grown to late log phase at 37° C. (18-24 hours). The bacteria were harvested by centrifugation and extracted following the method of Lancefield (Wilkinson, H. W., Facklam, R. R., Wortham, E. C. [1973] Infect. Immun. 8:228). Essentially, the bacterial pellet was resuspended in approximately 1 ml 0.2N HCl in 0.85% NaCl. These suspensions were boiled for 10 minutes then adjusted to neutral pH by the addition of 0.2N NaOH. Suspensions were centrifuged at 10,000 xg for 30 minutes to remove bacterial debris and the supernatants were decanted.

Precipitin Assay for Typing Group B Streptococci

Hot acid extracts were reacted with antisera of appropriate specificity and reactivity determined by precipitation in capillary tubes or by radial immunodiffusion in agarose gel (Jensen, N. E. [1979] Acta Path. Microbiol. Scand. 87:77-83).

Immunoelectrophoresis

Hot acid extracts of GBS strains were concentrated 10-fold using a Minicon macrosolute concentrator (Amicon, Danvers, Mass.). The concentrated hot acid extracts were applied to the wells of an agarose plate (Hyland Diagnostics Agarose Gel IEP System, Malvern, Pa.) which was then subjected to electrophoresis at 30 mAmps for 40 minutes. The agarose from the pre-cut troughs was removed and anti-c protein marker typing serum was applied. The plates were incubated overnight at 4° C. in a moist chamber. After being soaked in PBS, pH 7.2, for 48 hours and in deionized water for 12 hours, the plates were stained with 0.7% amido black in 7% acetic acid for 5 minutes. Destaining was done with 7% acetic acid until all background color was removed.

Radioimmunoassay for Determination of Subtypes of Group B Streptococcal Strains A two-stage radioimmunoassay (RIA) was employed to detect type specific antigens on the bacterial cell surface. Laboratory strains were inoculated into 10 ml Todd-Hewitt broth starter culture tubes and grown to late log phase at 37° C. (18 to 24 hours). The bacteria were pelleted by centrifugation for 8 minutes at 1,000 xg, and the bacterial pellets were resuspended in 2 ml PBS, pH 7.4. Tubes containing 100 μl of bacterial suspension were incubated for 1 hour at 37° C. with 100 μl of a 1:400 dilution of each type specific antiserum; anti-Ia, anti-Ib, anti-II, anti-III or anti-c antibody following selective adsorption. Normal rabbit serum was included in each assay as a control for specificity. Following incubation, the tubes were centrifuged for 8 minutes at 1,000 xg and the bacterial pellet washed with 2 ml PBS, pH 7.2, to remove unbound antibodies. The pellets were resuspended after the wash by vortexing, and bacterial-bound antibody was quantitated by addition of 100 μl of $^{125}I$ labeled Protein A containing approximately 30,000 cpm. This Fc receptor has a high affinity for rabbit immunoglobulin and, therefore, binds to any bacterial-associated antibodies. The tubes were incubated for 1 hr at 37° C. and the bacterial pellets washed twice with 2 ml of metal-free VBS containing 0.01M ethylenediaminetetraacetic acid (EDTA) and 0.1% gelatin (EDTA-gel) to remove any labeled tracer not associated with a bacterial antigen-antibody complex. The bacterial-associated radioactivity was quantitated in a Beckman 5500 auto-gamma counter. The background level of radioactivity was determined to control tubes containing bacteria and radiolabeled Protein A only. Since the expression of a bacterial receptor that would bind antibody molecules non-specifically would complicate our assay, we have included a normal rabbit serum control in all of our assays.

Following are examples which illustrate procedures, including the best mode, for practicing the invention. These examples should not be construed as limiting. All percentages are by weight and all solvent mixture proportions are by volume unless otherwise noted.

EXAMPLE 1

Testing of GBS Strains

Fifty-three group B streptococcal (GBS) strains were tested for the presence of type specific carbohydrate antigens and protein antigens by the two-stage radioimmunoassay (RIA) described in the Methods. These strains were also typed by the conventional precipitin test of hot acid extracts, with reactivity detected by radial immunodiffusion as described in the Methods. There was an absolute correlation between the carbohydrate antigens detected by each assay (see Table 1). Strain HG782 was particularly interesting because it demonstrated two carbohydrate antigens. This was originally believed to be a mixture of two strains. Consequently, the RIA was repeated on cultures of fifteen individual colonies from this isolate and identical results were obtained.

FIG. 1 shows the analysis of type specific carbohydrate antigen on the surface of Group B streptococci using the two-stage radioimmunoassay outlined in the Methods. The height of each line depicts the amount of $^{125}I$ Fc receptor associated with each strain minus the background radioactivity, thus giving a measure of the quantity of each specific antiserum associated with the bacterial pellet. A comparison of the results obtained using this assay and the classical precipitin assays are presented in Table 1. The results presented in FIG. 1 demonstrate that variation in the quantities of type specific carbohydrate antigens expressed on various strains was detected by the two-stage RIA. The results obtained by the RIA were reproducible from day to day with each strain being typed on at least two occasions with identical results. In contrast to the semi-quantitative results obtained by RIA, precipitin tests of hot acid extracts indicated only the presence of a given carbohydrate.

EXAMPLE 2

Characterizing Antigens Within the c Protein Marker Complex

When the two approaches, described in Example 1, were applied to characterizing antigens within the c protein marker complex, a much more complicated pattern emerged. Reactivity with antisera against the c protein complex was detected by RIA in 36/53 strains and by precipitin test in 20/53 strains (see Table 2). In order to analyze the reasons for these differences, the two-stage RIA was repeated with a series of anti-c protein antisera which had been selectively adsorbed with bacteria showing different c protein reactivity profiles (see FIGS. 2a and 2b).

Figure 2A:
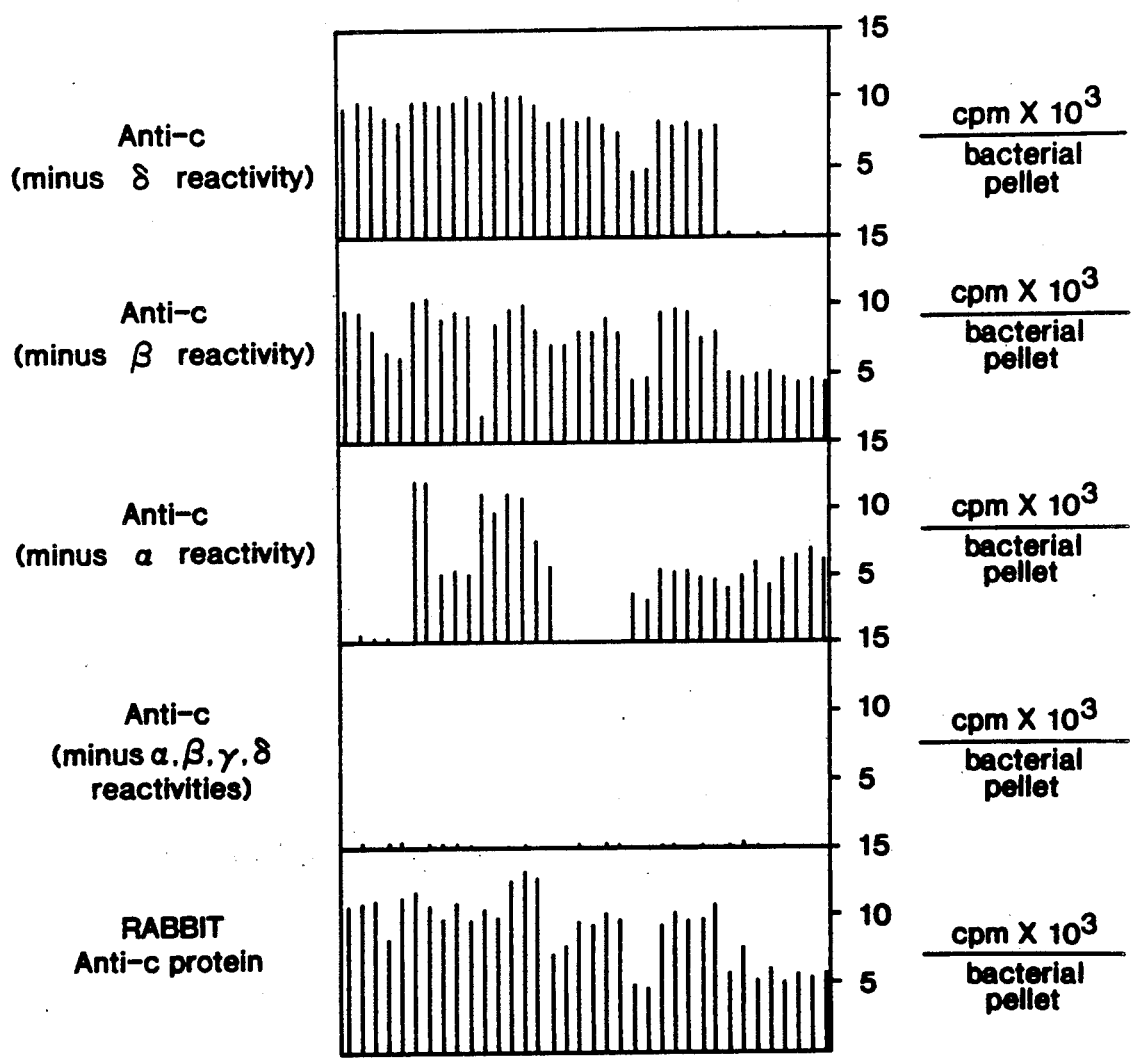
FIG. 2a: Analysis of c protein antigens on the surface of group B streptococci.
Figure 2B:
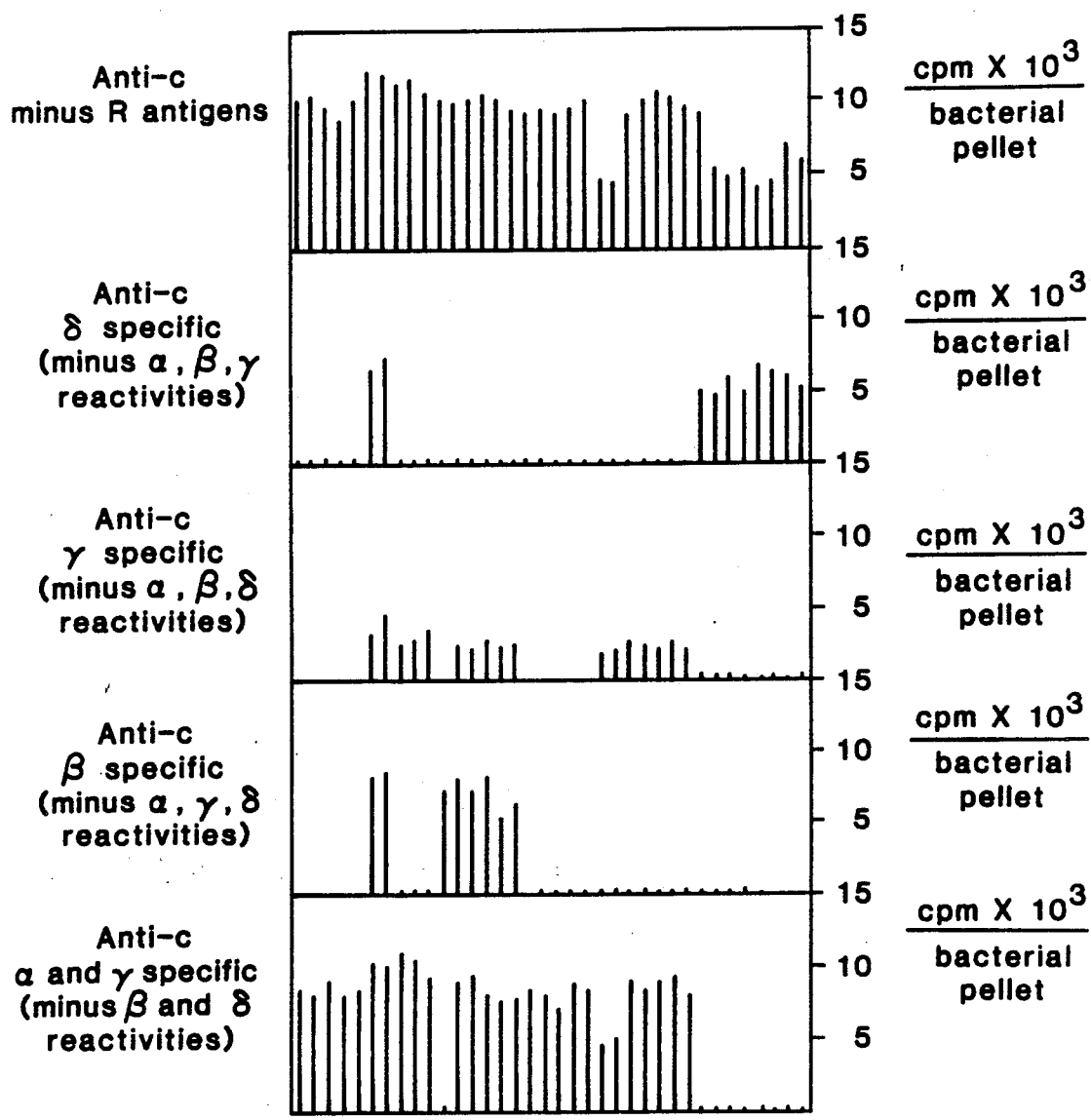
FIG. 2b: Further analysis of unique antigens within the c protein marker complex.

FIG. 2a shows the analysis of c protein antigens on the surface of group B streptococci using the two-stage radioimmunoassay. The antiserum used in the assays is either the unabsorbed anti-c antiserum (bottom panel) or the same antiserum that has been adsorbed with selective bacteria demonstrating unique reactivities as detailed in Table 3. The height of each line depicts the amount of $^{125}I$ labeled bacterial Fc receptor associated with each strain minus the background radioactivity, thus giving a measure of the quantity of each specific antiserum associated with the bacterial pellet. FIG. 2a shows further analysis of unique antigens within the c protein marker complex using antisera selective for $\alpha, \beta, \gamma$, and $\delta$ antigens of the c protein marker complex. These specific antisera were prepared by selective adsorption of the CDC anti-c typing serum as described in Table 3. Using this approach a variety of distinct binding patterns were observed which could be accounted for by a minimum of four separate epitopes. The bacteria were also tested with anti-c antisera which had been adsorbed with the group A strain R-28 demonstrating that none of the reactivities detected were due to the R protein antigen (see FIG. 2b).

EXAMPLE 3

Expression of Antigens by Strain A909-ATCC 27591

The A909 strain expressed all four reactivities as detected by the RIA. This is the Lancefield prototype Ia/c strain which is used by CDC to prepare the c protein typing antiserum used in this study. In an attempt to identify the nature of the reactive antigens, a 10-fold concentrated hot acid extract of this strain was analyzed by immunoelectrophoresis (IEP) (see FIG. 3).

Figure 3:
FIG. 3: Immunoelectrophoresis of extract of prototype Ia/c strain A909.

FIG. 3 shows immunoelectrophoresis of a tenfold concentrate of a hot acid extract of prototype Ia/c strain A909, developed against polyclonal rabbit anti-c protein marker typing serum. Two of the resulting precipitin arcs correspond to the previously reported $\alpha$ and $\beta$ antigens observed by Bevanger (Bevanger, L. and Iversen, O.-J. [1981] Acta Path. Microbiol. Scand. 89:205-209). In addition, a precipitation line corresponding to a third reactivity was observed (see FIG. 3). This antigen corresponded to the $\gamma$ reactivity demonstrated by RIA. The $\gamma$ epitope has not been detected by IEP in the past and can only be seen after concentration of the hot acid extracts. The fourth reactivity, $\delta$, could not be detected by IEP even when hot acid extracts were concentrated 50-fold. The inability of hot acid extracts of $\delta$-bearing strains to competitively inhibit the $\delta$-reactivity in the two-stage RIA indicates that either $\delta$ is not acid-extractable or it is acid labile. In contrast, solubilized antigens present in hot acid extracts of $\alpha$, $\beta$, and $\gamma$ bearing strains were able to inhibit those corresponding reactivities in the two-stage RIA.

These results suggest that the c protein marker complex represents a more complicated antigenic structure than has been recognized previously. Furthermore, since the precipitin test is a qualitative one and is dependent on optimal concentrations of antigen and type specific antisera, low levels of one or more components of the c protein complex may lead to false negative results However, low levels of any surface antigen would be detectable in the more sensitive RIA.

EXAMPLE 4

Preparation of Monospecific Antisera

Monospecific antisera against $\beta$, $\gamma$, and $\delta$ epitopes have been prepared by selective absorption with combinations of strains bearing all other reactivities (see Table 3). Streptococcus agalactiae strains PF65BV, PF549AR-B, TC795 and Pehierew (PEH) were deposited with the American Type Culture Collection, 12301 Parklawn Drive, Rockville, Md. 20852 U.S.A., on June 10, 1991 and were assigned the accession numbers ATCC 55191, ATCC 55192, ATCC 55193 and ATCC 55194, respectively. Specific antisera against c could not be generated since we were unable to find a strain that expressed $\gamma$ that did not also express $\alpha$. Strains expressing $\alpha$ alone could be identified by comparison of results using $\gamma$ specific, versus plus $\gamma$ specific, antisera. Each of the 53 strains was characterized based on its reactivity with each of the individual carbohydrate typing antisera, as well as the polyclonal unabsorbed, and monospecific absorbed, anti-c protein complex typing sera (see Tables 1 and 2).

EXAMPLE 5

Summary of Incidence of Antigens

Table 4 summarizes the incidence of each antigen detected by the two-stage RIA. There were 2/53 strains found to have no type specific carbohydrate. Type Ia and Ib antigens were each detected on 9/53 strains and type II and III antigens were each seen on 16/53 strains. As mentioned, one strain bears both type II and III antigens. At least one component of the c protein marker complex was seen on 68% or 36/53 of the group B streptococcal strains tested by RIA. The $\alpha$ antigen was the most widely detected epitope and was present on 27/53 strains. A subset of strains bearing the $\alpha$ antigen expressed the $\gamma$ reactivity. Seventeen of the 27 $\alpha$-positive strains expressed the $\gamma$ epitope which was never detected on a strain that did not also have the $\alpha$ antigen. The $\delta$ reactivity was detected on 10 strains. With the exception of the two strains which bear all four RIA reactivities (both type Ia/c), this epitope was detected only on type III strains and was the only c protein component associated with these strains. The $\beta$ antigen was the least common c protein reactivity found on GBS and was detected on the surfaces of 8/53 strains screened.

EXAMPLE 6

Testing a Clinical Specimen

A clinical specimen, for example, body fluids, swabs of tissue and tissue itself, and the like can be tested, for example, in accord with the following procedures:

1. Vaginal cultures can be obtained with Culturette II ™ dual swabs (Marion Scientific Corp., Kansas City, Mo.);

2. Inoculate each swab into 2 ml Lim Group B Strep Broth ™ (Gibco Laboratories, Madison, Wis.) and incubate for at least 6 hours at 37° C.;

3. Test broth cultures for GBS by slide coagglutination (Phadebact Strep B ™ test, Pharmacia Diagnostics, Piscataway, N.J.);

4. Isolate GBS by streaking onto Blood Agar Plates (Difco);

5. Inoculate isolated GBS colonies into 10 ml Todd-Hewitt broth tubes and incubate for 6 to 24 hours at 37° C.; and 6 Conduct two stage RIA as described in the Materials and Methods section, supra.

Other examples of clinical specimens are cerebral spinal fluid, amniotic fluid, cervical swabs, blood, lung lavage, urethral swabs, rectal swabs, throat swabs, umbilical swabs, saliva, and the like.

The subject invention can be used to identify and quantify native antigens on potentially pathogenic group B streptococci bacteria present in clinical specimens of mammals, for example, humans and cows. Particularly important are pregnant mammals.

In addition to the previously-described uses, the subject invention also is useful for epidemiological studies. For example, the invention can be used to trace zoonotic sources of group B streptococcal outbreaks. Further, the invention can be used to trace nosocomial sources of group B streptococcal outbreaks in hospitals, in particular, newborn nurseries. Further, there may be as yet undiscovered biological properties of the novel $\gamma$ and $\delta$ antigens described herein, analogous to the ability of the $\beta$ antigen to bind IgA, which would impact on their capacity to cause disease.

The novel antisera of the subject invention can be employed in a variety of immunotechnology procedures. The antisera can be immobilized and tagged with an appropriate label, such as a radioisotope, an optical label, e.g., a fluorescent tag, an enzyme, an electron dense ligand, and the like. The label may be detected by a gamma counter if the label is a radioactive gamma emitter, or by a fluorimeter, if the label is a fluorescent material. In the case of an enzyme, label detection may be done colorimetrically employing a substrate for the enzyme. All of these procedures are well known in the art. See "Applications of Bacterial Fc Receptors in Immunotechnology," Boyle, Michael D. P., BioTechniques Nov./Dec. 1984, pp. 334-339. This publication and the publications recited therein are incorporated herein by reference thereto.

Immobilization supports or substrates which can be used in the subject invention processes are any inert material generally used in immunochemical assays. Examples of such materials are beads formed of glass, polystyrene, polypropylene, dextran or other material. Other suitable solid phases include tubes or plates formed from or coated with these materials. Commercially available supports are agarose beads, IMMUNOBEADS ® and AFI-GEL ® 15 activated beads. These are all trademarks of Bio-Rad, Richmond, Calif.

The antisera of the invention can be utilized in any immunoassay method which involves the ability of an antibody to recognize or react with an antigen or antigenic determinant (epitope) and the detection or assay of the resulting antigen-antibody complex.

As disclosed previously, the components to be assayed may be coupled or bonded to any assayable ligand such as a radioisotope, fluorescent tag, bio-assayable enzyme, electron dense tag, and the like. Those skilled in the art, having been exposed to the principles of the present invention, will be cognizant of the types of assayable ligands and methods for coupling them to the components of the methods of the present invention without the exercise of undue experimentation or inventive faculties.

For convenience and standardization, reagents for the performance of the assay can be assembled in assay kits. Two types of kits can be used.

One kit would provide for the rapid detection of unique antigens in which immobilized antiserum to native components within the c protein marker complex, for example, $\alpha$, $\beta$, $\gamma$, and $\delta$, are mixed with group B streptococcal bacteria and agglutination is measured. A positive agglutination reaction indicates the presence of the corresponding antigen to the immobilized antibody. Thus, this type of kit would contain (a) immobilized antiserum;

(b) a culture of intact group B streptococcal bacteria;

(c) a negative control using immobilized normal serum; and (d) a positive control using bacteria known to express the desired antigen.

Another type of kit uses immobilized antigens from the c protein marker complex to quantify levels of specific antibodies. This testing can be used to identify individuals having a potential risk for infection by group B streptococcal bacteria carrying the particular antigen. This type of kit would contain (a) immobilized antigen;

(b) test serum (clinical specimen);

(c) Fc reporter, e.g., a radioisotope, an optical label, an enzyme, an electron dense ligand, and the like;

(d) normal serum control (no antibodies to any c protein marker); and (e) positive control containing specific antibody to the corresponding immobilized antigen.

If the label is an enzyme, an additional element of the kit can be the substrate for the enzyme.

Examples of enzymes which can be used as a label are lactoperoxidase, horse-radish peroxidase, alkaline phosphatase, glucose oxidase or $\beta$-glucuronidase.

Examples of radioisotope labels which can be used are $^{125}I$, $^{131}I$, $^{3}H$, $^{14}C$ or $^{35}S$.

Examples of electron dense ligand labels which can be used are ferritin, gold or horse-radish peroxidase.

TABLE 1

Summary of Precipitin Assay and Two Stage Radioimmunoassay to Type Group B Streptococci for Carbohydrate Antigens

| Strain | Detected by Precipitin Test | Detected by RIA |
|---|---|---|
| N86K | No type | No type |
| NP1AR | No type | No type |
| HG824 | Ia | Ia |
| SS617 | Ia | Ia |
| HG346 | Ia | Ia |
| PF534AR | Ia | Ia |
| J46 | Ia | Ia |
| HG783 | Ia | Ia |
| HG784 | Ia | Ia |
| HG381 | Ia | Ia |
| A909 | Ia | Ia |
| HG812 | Ib | Ib |
| HG806 | Ib | Ib |
| 2AR | Ib | Ib |

TABLE 1-continued
Summary of Precipitin Assay and Two Stage Radioimmunoassay to Type Group B Streptococci for Carbohydrate Antigens

| Strain | Detected by Precipitin Test | Detected by RIA |
|---|---|---|
| TC795 | Ib | Ib |
| PF549AR-B | Ib | Ib |
| HG805 | Ib | Ib |
| HG769 | Ib | Ib |
| TC137 | Ib | Ib |
| SS618 | Ib | Ib |
| HG811 | II | II |
| PF58AV | II | II |
| PF536AR | II | II |
| PF549AR-NB | II | II |
| PF541AR | II | II |
| J44 | II | II |
| PF65BV | II | II |
| PF610AR | II | II |
| NPF1AV | II | II |
| HG818 | II | II |
| HG819 | II | II |
| 9B200 | II | II |
| HG768 | II | II |
| HG804 | II | II |
| HG774 | II | II |
| HG782 | II | II,III |
| HG820 | III | III |
| VC75 | III | III |
| HG780 | III | III |
| HG757 | III | III |
| HG814 | III | III |
| HG754 | III | III |
| HG802 | III | III |
| HG738 | III | III |
| J48 | III | III |
| J52 | III | III |
| PEH | III | III |
| J51 | III | III |
| HG786 | III | III |
| HG828 | III | III |
| HG770 | III | III |
| HG771 | III | III |

TABLE 2
$a$ of $\alpha$, $\beta$, $\gamma$, and $\delta$ Antigens on Strains Reactive with Anti-c Typing Antisera Detected by RIA

| Strain | Carbohydrate Subtype | c Protein Reactivity Detected by Precipitin Test | c Protein Marker Antigens Detected by RIA |
|---|---|---|---|
| HG346 | Ia | + | $\alpha$ |
| PF534AR | Ia | + | $\alpha$ |
| J46 | Ia | + | $\alpha$ |
| HG783 | Ia | − | $\alpha$ |
| HG784 | Ia | − | $\alpha$ |
| HG381 | Ia | + | $\alpha,\beta,\gamma,\delta$ |
| A909 | Ia | + | $\alpha,\beta,\gamma,\delta$ |
| HG812 | Ib | + | $\alpha,\gamma$ |
| HG806 | Ib | + | $\alpha,\gamma$ |
| 2AR | Ib | + | $\alpha,\gamma$ |
| TF795 | Ib | + | $\beta$ |
| PF549AR-B | Ib | + | $\alpha,\beta,\gamma$ |
| HG805 | Ib | + | $\alpha,\beta,\gamma$ |
| HG769 | Ib | + | $\alpha,\beta,\gamma$ |
| TC137 | Ib | + | $\alpha,\beta,\gamma$ |
| SS618 | Ib | + | $\alpha,\beta,\gamma$ |
| J44 | II | + | $\alpha$ |
| PF65BV | II | + | $\alpha$ |
| PF25AR | II | + | $\alpha$ |
| PF610AR | II | + | $\alpha$ |
| NPF1AV | II | + | $\alpha$ |
| HG818 | II | − | $\alpha,\gamma$ |
| HG819 | II | − | $\alpha,\gamma$ |
| 9B200 | II | + | $\alpha,\gamma$ |
| HG768 | II | − | $\alpha,\gamma$ |
| HG804 | II | − | $\alpha,\gamma$ |
| HG774 | II | − | $\alpha,\gamma$ |

TABLE 2-continued
$a$ of $\alpha$, $\beta$, $\gamma$, and $\delta$ Antigens on Strains Reactive with Anti-c Typing Antisera Detected by RIA

| Strain | Carbohydrate Subtype | c Protein Reactivity Detected by Precipitin Test | c Protein Marker Antigens Detected by RIA |
|---|---|---|---|
| HG782 | II,III | − | $\alpha,\gamma$ |
| J48 | III | − | $\delta$ |
| J52 | III | − | $\delta$ |
| JB3 | III | − | $\delta$ |
| J51 | III | − | $\delta$ |
| HG786 | III | − | $\delta$ |
| HG828 | III | − | $\delta$ |
| HG770 | III | − | $\delta$ |
| HG771 | III | − | $\delta$ |

TABLE 3
Depletion of Component Reactivities from Anti-Ibc Typing Antiserum

| Strain(s) Used For Adsorption | Reactivities Depleted | Reactivities Remaining |
|---|---|---|
| R-28 (Group A) | R | $\alpha,\beta,\gamma,\delta$ |
| PF65BV | $\alpha$ | $\beta,\gamma,\delta$ |
| TC795 | $\beta$ | $\alpha,\gamma,\delta$ |
| J48 | $\delta$ | $\alpha,\beta,\gamma$ |
| TC795,PEH | $\beta,\delta$ | $\alpha,\gamma$ |
| 9B200,PEH | $\alpha,\gamma,\delta$ | $\beta$ |
| PF65BV,TC795,J48 | $\alpha,\beta,\delta$ | $\gamma$ |
| PF549AR-B | $\alpha,\beta,\gamma$ | $\delta$ |
| HG381 | $\alpha,\beta,\gamma,\delta$ | NONE |

TABLE 4
Summary of Typing Results (53 strains)

| Carbohydrate Antigens | No. | % of All Strains | % of Ic strains |
|---|---|---|---|
| No Type | 2 | 3.8 | |
| Ia | 9 | 16.0 | |
| Ib | 9 | 17.0 | |
| II | 16 | 30.2 | |
| III | 16 | 30.2 | |
| II/III | 1 | 1.9 | |
| Ic protein marker | 36 | 67.9 | 100.0 |
| $\alpha$ | 27 | 50.9 | 75.0 |
| $\beta$ | 8 | 15.1 | 22.2 |
| $\gamma$ | 17 | 32.1 | 47.2 |
| $\delta$ | 10 | 18.9 | 27.8 |

We claim:

1. An in vitro process for identifying and quantifying $\gamma$ or $\delta$ antigens on potentially pathogenic group B streptococci bacteria present in a clinical specimen which comprises:
   (a) contacting a suspension of cultured organisms from a clinical specimen with a preparation of monospecific antiserum against $\gamma$ or $\delta$ epitopes in an amount effective for detecting the antigen;
   (b) incubating the suspension to allow the formation of specific antigen-antibody complex;
   (c) centrifuging said suspension of group B streptococci to obtain a bacterial pellet containing antibody immobilized by binding to its cognate antigen on the cell surface;
   (d) washing said bacterial pellet to remove unbound antibodies;
   (e) resuspending said washed bacterial pellet and bound antibody and contacting said suspension with a labeled bacterial Fc receptor protein in an amount effective for detection of the bacterial-bound antibody;

(f) incubating said washed bacterial pellet and then washing to remove any labeled tracer not associated with bacterial antigen-antibody complex; and (g) measuring the activity of the bacteriral-associated label by means appropriate for detecting label activity to identify and quantitate the type-specific antigens.

2. The process, according to claim 1, wherein said clinical specimen is selected from the group consisting of vaginal swabs, cerebral spinal fluid, amniotic fluid, cervical swabs, blood, lung lavage, urethral swabs, rectal swabs, umbilical swabs, and saliva.

3. The process, according to claim 1, wherein said clinical specimen is a vaginal culture.

4. The process, according to claim 3, wherein said vaginal culture is obtained from a mammal.

5. The process, according to claim 4, wherein said mammal is a pregnant mammal.

6. The process, according to claim 5, wherein said pregnant mammal is a pregnant human.

7. Monospecific antiserum against the γ epitope, said γ epitope being a member of the c protein marker complex expressed by group B streptococci bacteria.

8. Monospecific antiserum against the δ epitope, said δ epitope being a member of the c protein marker complex expressed by group B streptococci bacteria.

9. A kit for rapid detection of γ and δ antigens on group B streptococci comprising:

(a) immobilized antiserum to γ or δ antigen markers;

(b) a negative control comprising immobilized normal serum which does not contain antibodies associated with group B streptococci; and (c) a positive control comprising bacteria known to express the desired antigen.

10. A kit for quantifying levels of specific antibodies to the γ or δ antigen on group B *streptococci* comprising:

(a) immobilized γ or δ antigen;

(b) labeled Fc receptor;

(c) normal serum which does not contain specific antibody, for negative control; and (d) positive control containing specific antibody to the corresponding immobilized antigen.

11. The kit, according to claim 9, wherein said immobilized antiserum comprises monospecific antiserum against the γ epitope, said epitope being a member of the c protein marker complex expressed by group B streptococci bacteria.

12. The kit, according to claim 9, wherein said immobilized antiserum comprises monospecific antiserum against the δ epitope, said epitope being a member of the c protein marker complex expressed by group B streptococci bacteria.

13. The kit, according to claim 10, wherein the label of said Fc receptor is selected from the group consisting of a radioisotope, an optical label, an enzyme, and an electron dense ligand.

14. The kit, according to claim 13, wherein said radioisotope is $^{125}I$, $^{131}I$, $^{3}H$, $^{14}C$ or $^{35}S$.

15. The kit, according to claim 13, wherein said enzyme is lactoperoxidase, horse-radish peroxidase, alkaline phosphatase, glucose oxidase, or β-glucuronidase.

16. The kit, according to claim 13, wherein said optical label is a fluorescent material.

17. The kit, according to claim 13, wherein said electron dense ligand is ferritin, gold, or horse-radish peroxidase.

18. The kit, according to claim 10, wherein said positive control comprises monospecific antiserum against the γ epitope, said epitope being a member of the c protein marker complex expressed by group B streptococci bacteria.

19. The kit, according to claim 10, wherein said positive control comprises monospecific antiserum against the δ epitope, said epitope being a member of the c protein marker complex expressed by group B streptococci bacteria.

* * * * *

UNITED STATES PATENT AND TRADEMARK OFFICE
CERTIFICATE OF CORRECTION

PATENT NO.    :    5,098,827

DATED         :    March 24, 1992

INVENTOR(S)   :    Michael D.P. Boyle and L. Jeanine Brady

It is certified that error appears in the above-identified patent and that said Letters Patent is hereby corrected as shown below:

Column 6   line 10: "results However" should read --results.  However--.
Column 6   line 25: "Specific antisera against c could not be" should read --Specific antisera against $\alpha$ could not be.
Column 6   line 29: "specific, versus plus $\gamma$ specific" should read --specific, versus $\alpha$ plus $\gamma$ specific,--
Column 9   line 41: "$\alpha$ of $\alpha$, $\beta$, $\gamma$ and" should read --Distribution of $\alpha$, $\beta$, $\gamma$ and--
Column 10  line 2: "$\alpha$ of $\alpha$, $\beta$, $\gamma$ and" should read -Distribution of $\alpha$, $\beta$, $\gamma$ and--
Column 11  line 6:  "the bacteriral-associated" should read --the bacterial-associated--.
Column 12  line 17: "of said Fc receptor" should read --of said labeled Fc receptor--.

Signed and Sealed this

Eighth Day of June, 1993

Attest:

MICHAEL K. KIRK

*Attesting Officer*        *Acting Commissioner of Patents and Trademarks*

UNITED STATES PATENT AND TRADEMARK OFFICE
CERTIFICATE OF CORRECTION

PATENT NO. : 5,098,827
DATED : Mar. 24, 1992
INVENTOR(S) : Michael D.P. Boyle, et al It is certified that error appears in the above-indentified patent and that said Letters Patent is hereby corrected as shown below:

Column 1, before Background of Invention: Insert --This invention was made with government support under NSF Grant No. DCB 8500512. The government has certain rights in this invention.--

Signed and Sealed this

Twenty-sixth Day of March, 1996

Attest:

BRUCE LEHMAN

Attesting Officer

Commissioner of Patents and Trademarks